US009072486B2

(12) United States Patent
Limmer et al.

(10) Patent No.: US 9,072,486 B2
(45) Date of Patent: Jul. 7, 2015

(54) C-ARM X-RAY DEVICE HAVING DRIVEN C-ARM BEARING ROLLERS

(75) Inventors: Andreas Limmer, Fürth (DE); Manfred Sechser, Neusorg (DE)

(73) Assignee: Siemens Aktiengesellschaft, München (DE)

( * ) Notice: Subject to any disclaimer, the term of this patent is extended or adjusted under 35 U.S.C. 154(b) by 343 days.

(21) Appl. No.: 13/490,304

(22) Filed: Jun. 6, 2012

(65) Prior Publication Data

US 2012/0314843 A1 Dec. 13, 2012

(30) Foreign Application Priority Data

Jun. 7, 2011 (DE) .................. 10 2011 077 086

(51) Int. Cl.
*H05G 1/02* (2006.01)
*A61B 6/02* (2006.01)
*A61B 6/00* (2006.01)

(52) U.S. Cl.
CPC ............... *A61B 6/4441* (2013.01); *H05G 1/02* (2013.01); *A61B 6/44* (2013.01)

(58) Field of Classification Search
CPC ............. H05G 1/00; H05G 1/02; A61B 6/00; A61B 6/02; A61B 6/44; A61B 6/4405; A61B 6/4429; A61B 6/4435; A61B 6/4441

USPC ................ 378/4–20, 193, 194, 197, 204, 210
See application file for complete search history.

(56) References Cited

U.S. PATENT DOCUMENTS

| 3,281,598 | A | * | 10/1966 | Hollstein ...................... 378/179 |
| 4,475,072 | A | * | 10/1984 | Schwehr et al. ............... 318/602 |
| 4,955,046 | A | | 9/1990 | Siczek et al. |
| 6,132,087 | A | * | 10/2000 | Kusch et al. .................. 378/197 |
| 6,599,017 | B2 | * | 7/2003 | Geelhoed et al. ............... 384/58 |
| 6,926,442 | B2 | * | 8/2005 | Stockl ........................... 378/197 |
| 2007/0280426 | A1 | * | 12/2007 | Saffer ........................... 378/198 |
| 2009/0296892 | A1 | | 12/2009 | Fadler et al. |

FOREIGN PATENT DOCUMENTS

| DE | 102004011460 | 10/2005 |
| DE | 102008026622 | 12/2009 |

OTHER PUBLICATIONS

German Office Action cited in German Application No. DE 10 2011 077 086.0, mailed Feb. 9, 2012.

* cited by examiner

*Primary Examiner* — Anastasia Midkiff
(74) *Attorney, Agent, or Firm* — Lempia Summerfield Katz LLC

(57) ABSTRACT

A C-arm x-ray device includes a C-arm and bearing rollers, on which the C-arm is moveably mounted. At least one drive unit drives or brakes the C-arm with the bearing rollers. The at least one drive unit is actively connected to the bearing rollers.

20 Claims, 2 Drawing Sheets

C-ARM X-RAY DEVICE HAVING DRIVEN C-ARM BEARING ROLLERS

This application claims the benefit of DE 10 2011 077 086.0, filed on Jun. 7, 2011.

BACKGROUND

The present embodiments relate to a C-arm x-ray device having a C-arm moveably mounted on bearing rollers.

C-arm x-ray devices may be used in medical diagnostics and therapy. A diagnosis or treatment device may be fastened to a C-shaped base body. On account of the shape, the C-arm with a diagnosis and/or treatment device may be moved in an orbital fashion around a point of a patient to be examined or treated, in order thus to reach different angular positions between the patient and diagnosis and/or treatment device without having to change the position of the patient.

X-ray apparatuses are distributed as diagnosis devices, with which an x-ray source is attached to one end of the C-arm, and an x-ray receiver and/or image amplifier is attached to the opposite end. The C-arm is mounted on rollers and may be pivoted about an orbital axis. A C-arm x-ray device of this type is described by way of example in DE 10 2004 011 460 A1.

In order to rotate the C-arm about the orbital axis in a motor-driven fashion, the U.S. Pat. No. 4,955,046 specifies a drive apparatus, with which a toothed belt connected to the C-arm is moved using a motor-driven toothed belt wheel. This provides that drive and braking forces may therefore be converted into a rotational movement of the C-arm using the toothed belt.

SUMMARY AND DESCRIPTION

The present embodiments may obviate one or more of the drawbacks or limitations in the related art. For example, a C-arm x-ray device and an associated method having a simple drive and/or braking apparatus of the C-arm are provided.

The present embodiments include directly driving and/or braking bearing rollers, upon which a C-arm is rotatably or moveably mounted. The bearing rollers are actively connected to a guide rail or a wire race and may therefore transmit acceleration forces to the C-arm using cohesion or adhesion.

A C-arm x-ray device includes a C-arm and bearing rollers, on which the C-arm is moveably mounted. The C-arm x-ray device also includes at least one drive unit (e.g., a drive unit) for moving and braking the C-arm with the bearing rollers. The drive unit is actively connected to the bearing rollers. The advantage of the present embodiments includes being able to save on drive shafts and deflection rollers.

In one embodiment, the bearing rollers are first bearing rollers, on which the C-arm is rotatably moveably mounted about an orbital axis. The drive unit is an orbital drive unit for rotating and braking the C-arm with the aid of the first bearing rollers. The orbital drive unit is actively connected to the first bearing rollers. In order to provide an effective transmission of power, at least two first bearing rollers are to be driven by the orbital drive unit.

In one embodiment, the orbital drive unit may include an electrical orbital motor.

In another embodiment, the orbital drive unit includes at least one first belt pulley that drives the orbital motor.

In yet another embodiment, the orbital drive unit includes at least one first belt. The first belt pulley moves the at least one first belt.

In one embodiment, the first belt may be actively connected to at least one first bearing roller such that the first belt transmits power to the first bearing roller.

In one embodiment, the C-arm x-ray device includes a first guide rail or a first wire race on a surface of the C-arm facing the first bearing rollers. The first bearing rollers are actively connected to the first guide rail or to the first wire race.

In another embodiment, the bearing rollers are second bearing rollers, on which the C-arm is moveably mounted in the horizontal direction. The drive unit is a horizontal drive unit for moving and braking the C-arm with the second bearing rollers. The horizontal drive unit is actively connected to the second bearing rollers.

In yet another embodiment, the horizontal drive unit includes an electrical horizontal motor.

In another embodiment, the horizontal drive unit includes at least one second belt pulley. The horizontal motor drives the at least one second belt pulley.

In one embodiment, the horizontal drive unit includes at least one second belt. The second belt pulley moves the at least one second belt.

In one embodiment, the first belt may be actively connected to at least one second bearing roller such that the first belt transmits power to the second bearing roller.

The C-arm x-ray device may include a second guide rail or a second wire race. The second bearing rollers are actively connected to the second guide rail or the second wire race.

Motors or brakes may also be directly connected to the bearing rollers, so that no belts and belt pulleys are needed. No gear reduction is interposed between the motor and/or brake and roller.

A method for driving and braking a C-arm of a C-arm x-ray device having bearing rollers, on which the C-arm (5) is moveably mounted, includes driving and/or braking, using the bearing rollers, the C-arm by the C-arm and the bearing rollers being actively connected with respect to one another.

In one embodiment, the bearing rollers are first bearing rollers, on which the C-arm is pivoted about an orbital axis. The C-arm with the first bearing rollers is rotated or braked by the C-arm and the first bearing rollers being actively connected.

In another embodiment, the bearing rollers are second bearing rollers, on which the C-arm is moved horizontally. The C-arm with the second bearing rollers is moved or braked.

DETAILED DESCRIPTION OF THE DRAWINGS

Figure 1:
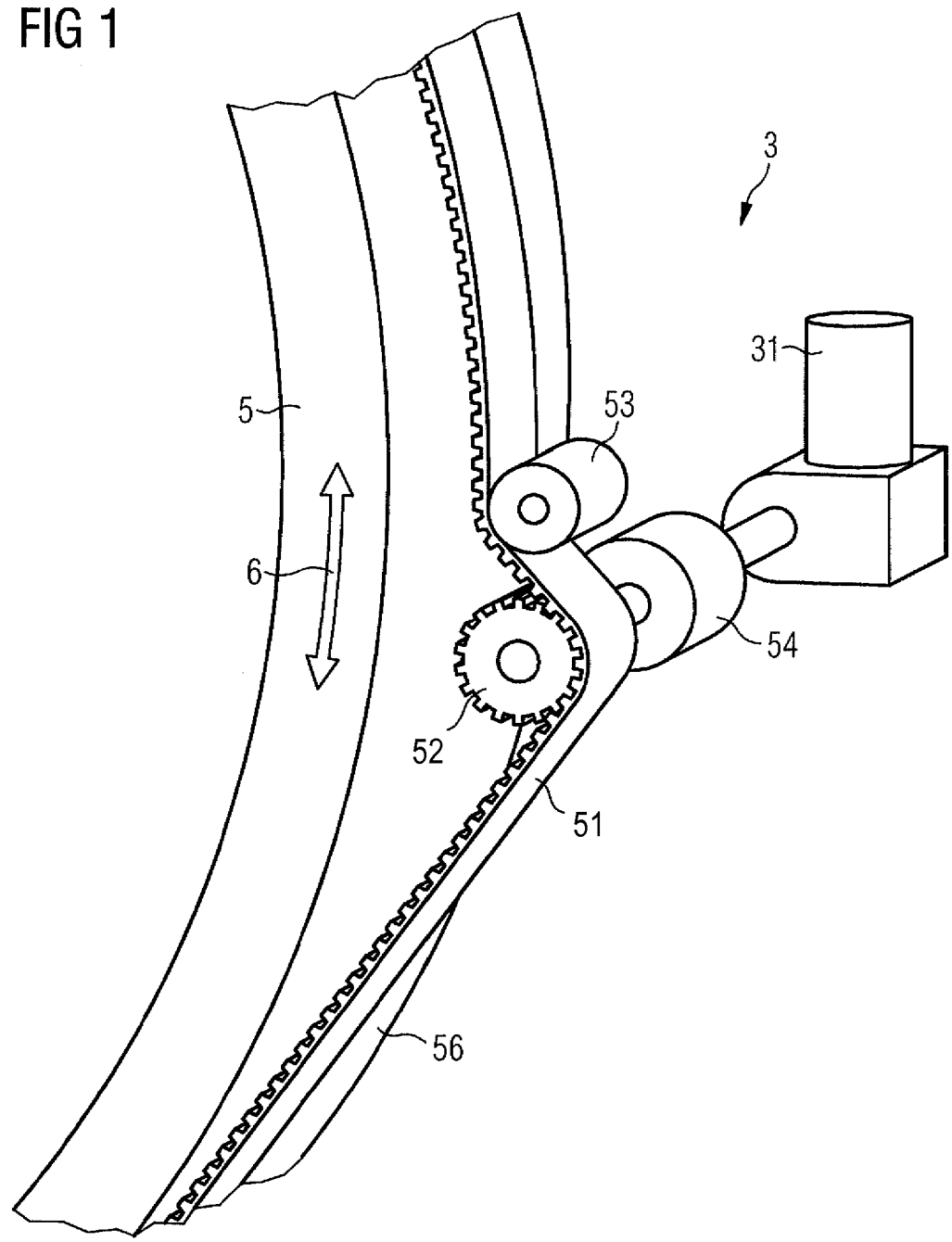
FIG. 1 shows a C-arm having a drive according to the prior art.

FIG. 1 shows an exemplary motor-driven orbital drive 3 of a C-arm 5, as specified in the U.S. Pat. No. 4,955,046. The orbital drive 3 includes an electrical orbital motor 31 that drives a toothed belt wheel 52 by way of a clutch 54. A toothed belt 51 is guided by way of the toothed belt wheel 52. The toothed belt 51 is fixedly connected to two ends of the C-arm 5. A draw roll 53 provides that the toothed belt 51 is always in contact with the toothed belt wheel 52. A rotary movement of the orbital motor 31 is converted into a rotary movement of the C-arm 5. The rotary movement of the C-arm 5 pivots the C-arm 5 about an orbital axis.

Figure 2:
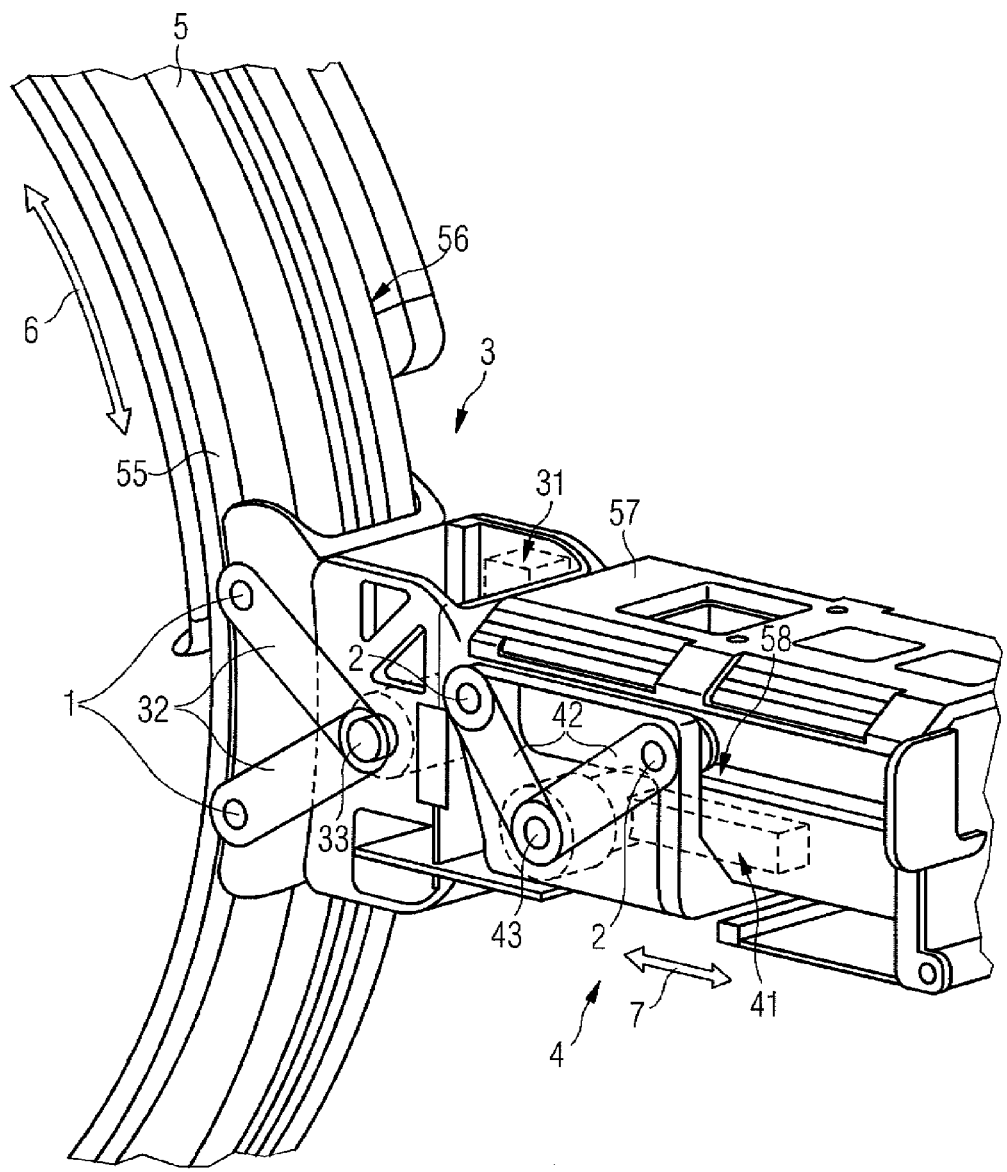
FIG. 2 shows one embodiment of a C-arm having a drive of bearing rollers.

FIG. 2 shows one embodiment of an orbital drive unit 3 and one embodiment of a horizontal drive unit 4 for a C-arm 5 of a C-arm x-ray device. Part of the C-arm 5 that is rotatably mounted on first bearing rollers 1 about an orbital axis is shown. The bearing rollers 1 run on a first guide rail 55 or a first wire race that is arranged on an exterior 56 of the C-arm 5. As a result, the C-arm 5 is guided about the orbital axis during rotation.

Two of the first bearing rollers 1 are driven and/or braked directly in each instance with a first belt 32 of the orbital drive unit 3. The first bearing rollers 1 are equipped, for example, with a groove for receiving the first belt 32. The first belt 32 runs on a drive side around a first belt pulley 33 that may be offset from an electrical orbital motor 31 in a rotational movement. The rotational movement of the orbital motor 31 is converted into a rotational movement of the C-arm 5 in direction 6 by the friction locking of the thus driven first bearing rollers 1 with the first guide rail 55. This is a distributed traction drive similar to that of a rail vehicle.

The braking forces of the orbital motor 31 may be transmitted to the C-arm 5 in a similar fashion. Alternatively, the braking forces may also be applied directly by disk brakes or shoe brakes attached to the first bearing rollers 1. In a further embodiment, the first bearing rollers 1 may be individually supplied in each instance with an electric motor.

FIG. 2 also shows second bearing rollers 2, on which a horizontal arm 57 is moveably mounted. With the aid of the horizontal arm 57, the C-arm fastened to the horizontal arm 57 may be moved in the horizontal direction 7. The second bearing rollers 2 run on a second guide rail 58 or a second wire race. The C-arm 5 is guided therethrough during a horizontal movement 7.

Two of the second bearing rollers 2 are driven and/or braked directly with a second belt 42 of the horizontal drive unit 4. The second bearing rollers 2 include, for example, a groove for receiving the second belt 42. On a drive side, the second belt 42 runs about a second belt pulley 43 that may be offset from an electrical horizontal motor 41 in one rotational movement. The rotational movement of the horizontal motor 41 is converted into a horizontal movement of the C-arm 6 in direction 7 by the friction locking of the thus driven second bearing rollers 2 with the second guide rail 58. This is a distributed traction drive similar to that of a rail vehicle.

The braking forces of the horizontal motor 41 may be transmitted to the horizontal arm 57 in a similar manner. Alternatively, the braking forces may also be applied directly by disk or shoe brakes attached to the second bearing rollers 2. In a further embodiment, the second bearing rollers 2 may each be supplied individually with an electric motor.

The first and second belts 32, 42 may be embodied as toothed belts. Alternatively, chains may also be used instead of belts.

According to the same principle, the C-arm may also be moved and braked (e.g., with directly driven bearing rollers) in other directions such as, for example, vertically.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A C-arm x-ray device comprising:
a C-arm;
bearing rollers, on which the C-arm is moveably mounted; and
at least one drive unit actively connected to the bearing rollers such that the C-arm is moveable and breakable with the bearing rollers.

2. The C-arm x-ray device as claimed in claim 1, wherein the C-arm is rotatably moveably mounted about an orbital axis on the bearing rollers,
wherein the at least one drive unit comprises an orbital drive unit operable to rotate and brake the C-arm with the bearing rollers, and
wherein the orbital drive unit is actively connected to the bearing rollers.

3. The C-arm x-ray device as claimed in claim 2, wherein the orbital drive unit includes an electrical orbital motor.

4. The C-arm x-ray device as claimed in claim 3, further comprising at least one belt pulley, the at least one belt pulley being driven by the electrical orbital motor.

5. The C-arm x-ray device as claimed in claim 4, further comprising at least one belt, the at least one belt pulley operable to move the at least one belt.

6. The C-arm x-ray device as claimed in claim 5, wherein the at least one belt is actively connected to at least one of the bearing rollers such that the at least one belt transmits power onto the at least one bearing roller.

7. The C-arm x-ray device as claimed in claim 2, further comprising a guide rail or a wire race on a surface of the C-arm facing one of the bearing rollers,
wherein the bearing rollers are actively connected to the guide rail or the wire race.

8. The C-arm x-ray device as claimed in claim 1, wherein the C-arm is moveably mounted in the horizontal direction on the bearing rollers,
wherein the at least one drive unit comprises a horizontal drive unit operable to move and brake the C-arm with the bearing rollers, and
wherein the horizontal drive unit is actively connected to the bearing rollers.

9. The C-arm x-ray device as claimed in claim 8, wherein the horizontal drive unit includes an electrical horizontal motor.

10. The C-arm x-ray device as claimed in claim 9, further comprising at least one belt pulley that the horizontal motor drives.

11. The C-arm x-ray device as claimed in claim 10, further comprising at least one belt, the at least one belt pulley operable to move the at least one belt.

12. The C-arm x-ray device as claimed in claim 11, wherein the at least one belt is actively connected to at least one of the bearing rollers such that the at least one belt transmits forces onto the at least one bearing roller.

13. The C-arm x-ray device as claimed in claim 8, further comprising a guide rail or a wire race,
wherein the bearing rollers are actively connected to the guide rail or the wire race.

14. The C-arm x-ray device as claimed in claim 12, further comprising a guide rail or a wire race,
wherein the bearing rollers are actively connected to the guide rail or the wire race.

15. The C-arm x-ray device as claimed in claim 3, further comprising a guide rail or a wire race on a surface of the C-arm facing one of the bearing rollers,
wherein the bearing rollers are actively connected to the guide rail or the wire race.

16. The C-arm x-ray device as claimed in claim 1, wherein the bearing rollers comprise first bearing rollers and second bearing rollers, wherein the C-arm is rotatably moveably mounted about an orbital axis on the first bearing rollers, wherein the at least one drive unit comprises an orbital drive unit operable to rotate and brake the C-arm with the first bearing rollers, and wherein the orbital drive unit is actively connected to the first bearing rollers, wherein the C-arm is moveably mounted in the horizontal direction on the second bearing rollers, wherein the at least one drive unit comprises a horizontal drive unit operable to move and brake the C-arm with the second bearing rollers, and wherein the horizontal drive unit is actively connected to the second bearing rollers.

17. The C-arm x-ray device as claimed in claim 4, further comprising a guide rail or a wire race on a surface of the C-arm facing one of the bearing rollers, wherein the bearing rollers are actively connected to the guide rail or the wire race.

18. A method for driving and braking a C-arm of a C-arm x-ray device including bearing rollers, on which the C-arm is moveably mounted, the method comprising:

driving and braking the C-arm with a drive unit and the bearing rollers, wherein the drive unit and the bearing rollers are actively connected.

19. The method as claimed in claim 18, wherein the C-arm is pivoted about an orbital axis on the bearing rollers, wherein the method further comprises rotating or braking the C-arm with the bearing rollers, and wherein the C-arm and the bearing rollers are actively connected.

20. The method as claimed in claim 18, wherein the C-arm is moved horizontally on the bearing rollers, and wherein the method further comprises moving or braking the C-arm with the bearing rollers.

* * * * *